US00PP26133P3

(12) United States Plant Patent
Li

(10) Patent No.: US PP26,133 P3
(45) Date of Patent: Nov. 24, 2015

(54) ***VERBENA* PLANT NAMED 'KLEVP12431'**

(50) Latin Name: ***Verbena* sp.**
Varietal Denomination: KLEVP12431

(71) Applicant: Klemm+Sohn GmbH & Co. KG, Stuttgart (DE)

(72) Inventor: Ruijun Li, North Parramata (AU)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 102 days.

(21) Appl. No.: 13/999,721

(22) Filed: Mar. 17, 2014

(65) Prior Publication Data

US 2015/0020260 P1 Jan. 15, 2015

(30) Foreign Application Priority Data

Jul. 3, 2013 (QZ) ..... PBR 2013/1833

(51) Int. Cl.
*A01H 5/00* (2006.01)
*A01H 5/02* (2006.01)

(52) U.S. Cl.
USPC ..... Plt./308
CPC ..... *A01H 5/02* (2013.01)

(58) Field of Classification Search
USPC ..... Plt./308
See application file for complete search history.

*Primary Examiner* — Annette Para
(74) *Attorney, Agent, or Firm* — James M. Weatherly; Bethany R. Roahrig; Cochran Freund & Young, LLC

(57) ABSTRACT

A new *Verbena* plant particularly distinguished by large purple and white flowers, excellent flower richness, early flowering time, a strong growth habit and good resistance to powdery mildew, is disclosed.

1 Drawing Sheet

Genus and species: *Verbena* sp.
Variety denomination: 'KLEVP12431'.

CROSS REFERENCE TO RELATED APPLICATIONS

This application claims, under 35 U.S.C. §119, priority to and the benefit of European Community Plant Variety Rights Application No. 2013/1833, filed Jul. 3, 2013, the entire contents of which are incorporated herein by reference for all purposes.

BACKGROUND OF THE NEW PLANT

The present invention comprises a new and distinct variety of *Verbena*, botanically known as *Verbena* sp., and hereinafter referred to by the variety name 'KLEVP12431'. 'KLEVP12431' originated from a cross-pollination conducted in April 2009 in Sydney, Australia between the proprietary female *Verbena* variety 'V 985' (unpatented), and the proprietary male *Verbena* variety derived from the cross of 'V 641' (unpatented)×'V 740' (unpatented).

The seeds from the cross were sown and plants were grown for evaluation, where an individual plant designated 'KLEVP12431' was selected from the group of plants in Cobitty, NSW, Australia in September, 2010.

In September 2010, 'KLEVP12431' was first vegetatively propagated by vegetative cuttings in Cobitty, NSW, Australia. 'KLEVP12431' was found to reproduce true to type in successive generations of asexual propagation via vegetative cuttings.

SUMMARY

The following are the most outstanding and distinguishing characteristics of this new variety when grown under normal horticultural practices in Stuttgart, Germany.

1. Large purple and white flowers;
2. Excellent flower richness;
3. Early flowering time;
4. A strong growth habit; and
5. Good resistance to powdery mildew.

DESCRIPTION OF THE PHOTOGRAPH

This new *Verbena* plant is illustrated by the accompanying photograph which shows the plant's overall plant habit including form, foliage, and flowers.

The photograph is of a two to three-month-old plant grown in a greenhouse in Stuttgart, Germany in May 2012. The colors shown are as true as can be reasonably obtained by conventional photographic procedures.

DESCRIPTION OF THE NEW VARIETY

The following detailed descriptions set forth the distinctive characteristics of 'KLEVP12431'. The data which define these characteristics were collected from asexual reproductions carried out in Stuttgart, Germany. Data was collected on three-month-old plants grown in a greenhouse in Stuttgart, Germany in February 2014. Color references are to The R.H.S. Colour Chart of The Royal Horticultural Society of London (R.H.S.)(2005).

Classification:

*Family*.—Verbenaceae.
*Botanical*.—*Verbena* sp.
*Common*.—*Verbena*.
*Designation*.—'KLEVP12431'.

Parentage:

*Female parent*.—The proprietary *verbena* variety 'V 985' (unpatented).

*Male parent*.—The proprietary male *verbena* variety derived from the cross of 'V 641' (unpatented)×'V 740' (unpatented).

Plant:

*Growth and branching habit*.—Upright.

*Height* (*from top of soil*).—30.0 cm.

*Width* (*horizontal plant diameter*).—30.0 cm.

*Time to produce a finished flowering plant*.—Approximately 8 weeks.

*Time to initiate and develop roots*.—3 weeks.

*Root description*.—White.

Stems:

*Number of branches per plant*.—More than 10.

*Growth habit*.—Semi-upright.

*Length*.—20.0 cm.

*Diameter*.—1.0 cm.

*Internode length*.—Approximately 2.0 cm.

*Color*.—RHS 130B.

*Anthocyanin*.—Absent.

*Texture and appearance*.—Pubescence, round.

Leaves:

*Arrangement*.—Opposite.

*Immature and mature leaf*.—Color: Upper surface: RHS 141A. Lower surface: RHS 141C.

*Length*.—2.5 cm.

*Width*.—1.5 cm.

*Shape*.—Lanceolate.

*Apex*.—Acute.

*Base*.—Obtuse.

*Margin*.—Crenate.

*Texture*.—Upper surface: Leathery. Lower surface: Rugose.

*Venation type*.—Pinnate.

*Venation color*.—Upper surface: RHS 141D. Lower surface: RHS 141D.

*Petioles*.—Length: 1.0 cm. Diameter: 0.1 cm. Color: RHS 141D. Texture: Leathery.

Flower buds:

*Shape*.—Tall, cylindrical.

*Length*.—0.5 cm.

*Diameter*.—0.1 cm.

*Color* (*at tight bud*).—RHS 59A.

Inflorescence:

*Blooming habit* (*flowering season*).—Continuously.

*Lastingness of individual blooms on the plant*.—2 weeks.

*Fragrance*.—Absent.

*Inflorescence type*.—Umbel.

*Length of inflorescence*.—6.0 cm.

*Diameter of inflorescence*.—6.0 cm.

*Number of florets per inflorescence*.—More than 15.

*Peduncle*.—Color: RHS 141A. Length: 4.0 cm. Diameter: 0.1 cm.

Florets:

*Length*.—2.0 cm.

*Diameter*.—4.0 cm.

*Texture*.—Glossy.

*Form*.—Umbel.

*Color*.—Immature: Upper surface: RHS 91D and RHS 999D. Lower surface: RHS 91D and RHS 999D. Mature: Upper surface: RHS 91C and RHS 999D. Lower surface: RHS 91C and RHS 999D.

*Corolla tube length*.—0.2 cm.

*Corolla tube color*.—RHS 91C.

*Petals*.—Length of lobe: 2.0 cm. Diameter of lobe: 2.0 cm. Lobe shape: Round. Apex: Acute. Base: Obtuse. Margin: Entire. Texture: Upper surface: Glossy, satiny. Lower surface: Glossy, satiny.

*Pedicels*.—Length: Approximately 1.0 cm. Diameter: 0.1 cm. Color: RHS 91C and RHS 999D. Texture and appearance: Hairy, dull. Arrangement: Round.

Sepals:

*Shape*.—Lanceolate.

*Apex*.—Acute.

*Base*.—Obtuse.

*Margin*.—Entire.

*Length*.—2.0 cm.

*Diameter*.—1.5 cm.

*Color*.—RHS 141C.

*Texture*.—Upper surface: Hairy, dull. Lower surface: Hairy, dull.

Reproductive organs:

*Stamens*.—Present.

*Quantity*.—Numerous.

*Filament length*.—0.1 cm.

*Filament diameter*.—Less than 0.1 cm.

*Anther*.—Shape: Elliptic. Color: RHS 141D. Length: Less than 0.1 cm. Diameter: Less than 0.1 cm.

*Pollen amount*.—Absent.

*Pistils*.—Number: 1. Length: 1.0 cm. Diameter: Less than 0.1 cm. Stigma: Color: RHS 141D. Appearance: Ovate. Length: Less than 0.1 cm. Diameter: Less than 0.1 cm. Style: Color: RHS 141D. Length: 0.2 cm. Diameter: Less than 0.1 cm. Appearance: Long.

Fruit and seed set: Seeds: None observed.

Disease and pest/insect resistance: Good tolerance against powdery mildew, very good weather resistance.

COMPARISON WITH PARENTAL LINES AND KNOWN VARIETIES

'KLEVP12431' is distinguished from its parents as described in Table 1.

TABLE 1

Comparison with Parental Lines

| Trait | Variety 'KLEVP12431' | Female parent 'V 985' | Male Parent 'V 641' × 'V 740' |
|---|---|---|---|
| Flower richness | Excellent | Good | Good |
| Earliness | Early | Early | Medium |

'KLEVP12431' is most similar to the commercial *verbena* Vepita 'Lavender White' (patent status unknown). Differences between the varieties are described in Table 2.

TABLE 2

| Comparison with Similar Variety | | |
|---|---|---|
| Trait | Variety 'KLEVP12431' | Commercial line Vepita 'Lavender White' |
| Flowering time | Earlier than Vepita 'Lavender White' | Late |
| Flower size | Bigger than Vepita 'Lavender White' | Smaller than 'KLEVP12431' |
| Growth habit | Stronger than Vepita 'Lavender White' | Weaker than 'KLEVP12431' |

TABLE 2-continued

| Comparison with Similar Variety | | |
|---|---|---|
| Trait | Variety 'KLEVP12431' | Commercial line Vepita 'Lavender White' |
| Resistance against powdery mildew | Better than Vepita 'Lavender White' | Not as good as 'KLEVP12431' |

I claim:

1. A new and distinct variety of *Verbena* plant designated 'KLEVP12431' as shown and described herein.

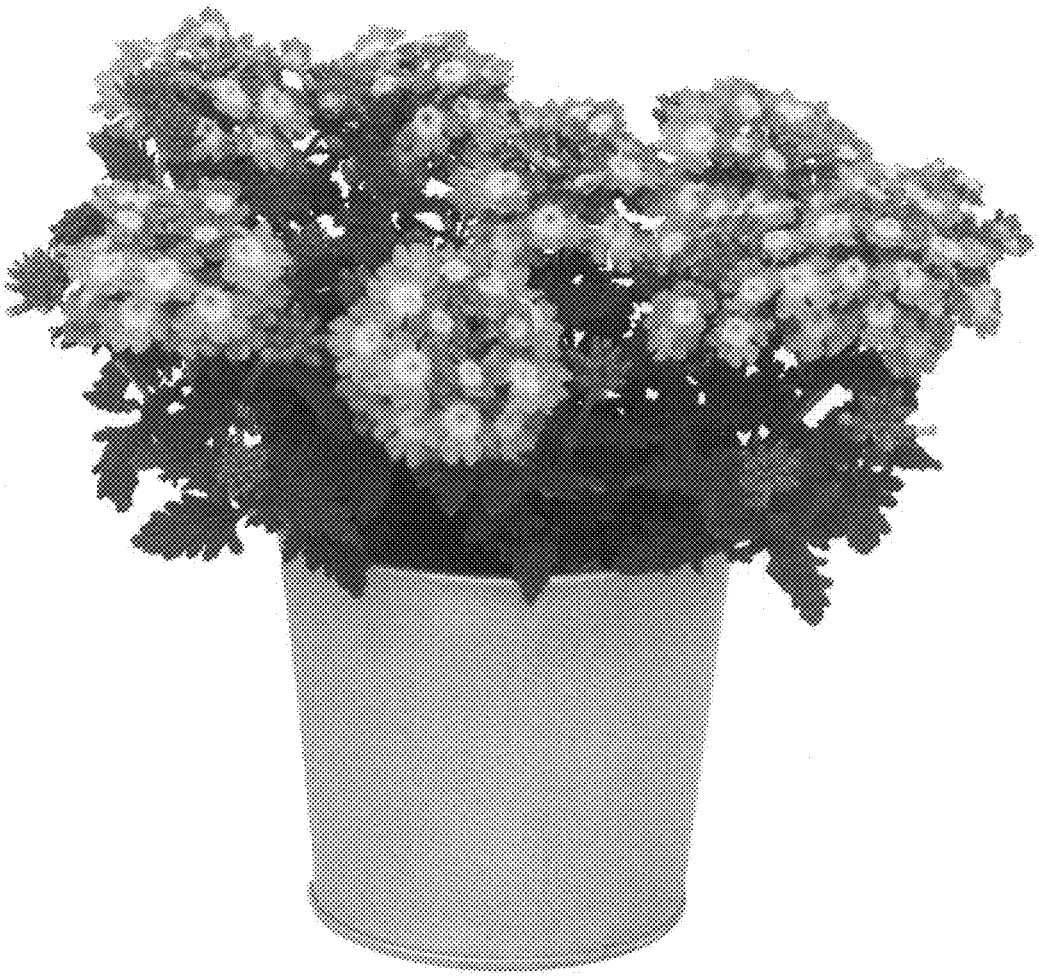

* * * * *